United States Patent
Schreieder et al.

(10) Patent No.: US 10,076,713 B2
(45) Date of Patent: Sep. 18, 2018

(54) METHOD AND APPARATUS FOR THE SEPARATION BY DISTILLATION OF A THREE- OR MULTI-COMPONENT MIXTURE

(71) Applicant: WACKER CHEMIE AG, Munich (DE)

(72) Inventors: Franz Schreieder, Tann (DE); Maximilian Aigner, Burghausen (DE); Jan Prochaska, Mehring (DE)

(73) Assignee: WACKER CHEMIE AG, Munich (DE)

(*) Notice: Subject to any disclaimer, the term of this patent is extended or adjusted under 35 U.S.C. 154(b) by 210 days.

(21) Appl. No.: 14/786,269

(22) PCT Filed: Mar. 26, 2014

(86) PCT No.: PCT/EP2014/056055
§ 371 (c)(1),
(2) Date: Oct. 22, 2015

(87) PCT Pub. No.: WO2014/173604
PCT Pub. Date: Oct. 30, 2014

(65) Prior Publication Data
US 2016/0074770 A1 Mar. 17, 2016

(30) Foreign Application Priority Data
Apr. 22, 2013 (DE) .......... 10 2013 207 282

(51) Int. Cl.
B01D 3/14 (2006.01)
C07F 7/12 (2006.01)

(52) U.S. Cl.
CPC ........... *B01D 3/141* (2013.01); *C07F 7/12* (2013.01); *C07F 7/121* (2013.01)

(58) Field of Classification Search
CPC .................................................. B01D 3/141
See application file for complete search history.

(56) References Cited

U.S. PATENT DOCUMENTS 4,419,188 A 12/1983 McCall
4,859,286 A 8/1989 Kaibel et al.
(Continued)

FOREIGN PATENT DOCUMENTS

CN 1678599 A 10/2005
CN 102316961 A 1/2012
(Continued)

OTHER PUBLICATIONS

Machine translation of WO 2006/008996. Obtained from WIPO website Oct. 18, 2017.*
(Continued)

*Primary Examiner* — Renee Robinson
(74) *Attorney, Agent, or Firm* — Brooks Kushman P.C.

(57) ABSTRACT

A method and apparatus for distillative separation of a mixture comprising three or more components including at least one low boiler, at least one medium boiler, and at least one high boiler, the method comprising feeding the mixture of three or more components to a first distillation column, removing the at least one high boiler as a bottom fraction from the first distillation column, feeding a top fraction of the first distillation column to a second distillation column, removing the at least one medium boiler via a sidestream takeoff from the second distillation column, removing the at least one low boiler as a top fraction from the second distillation column, and feeding a bottom takeoff stream from the second distillation column to the first distillation column as a reflux, wherein the first and the second distillation columns have vertical dividing walls.

14 Claims, 3 Drawing Sheets

(56) References Cited

U.S. PATENT DOCUMENTS

| | | | |
|---|---|---|---|
| 6,884,324 B2 | 4/2005 | Gutermuth et al. | |
| 2003/0106786 A1 | 6/2003 | Kaibel et al. | |
| 2004/0011706 A1 | 1/2004 | Kaibel et al. | |
| 2005/0252761 A1* | 11/2005 | Funke | B01D 3/141 203/29 |
| 2005/0258026 A1 | 11/2005 | Bassler et al. | |
| 2007/0227875 A1 | 10/2007 | Kammerhofer | |
| 2007/0293688 A1 | 12/2007 | Siegert et al. | |
| 2012/0048719 A1 | 3/2012 | Nuernberg et al. | |

FOREIGN PATENT DOCUMENTS

| | | | |
|---|---|---|---|
| DE | 19963017 A1 | 6/2001 | |
| DE | 100 21 703 A1 | 11/2001 | |
| DE | 102004040284 A1 | 2/2006 | |
| DE | 102008000490 A1 | 12/2008 | |
| EP | 1681094 A2 | 7/2006 | |
| JP | H0825915 B2 | 3/1996 | |
| JP | 2003220301 A | 8/2003 | |
| JP | 2006-36659 A | 2/2006 | |
| JP | 2009006240 A | 1/2009 | |
| WO | 2006/008996 A1 | 1/2006 | |
| WO | WO2006/008996 * | 1/2006 | C07C 29/80 |
| WO | 2009092682 A2 | 7/2009 | |
| WO | 2010/091492 A1 | 8/2010 | |

OTHER PUBLICATIONS

"Distillation columns with vertical partitions", Dipl.-Ing. Gerd Kaibel, vol. 10, Issue 1, 1987, pp. 92-98, https://doi.org/10.1002/ceat.270100112 (abstract provided).

* cited by examiner

Fig. 1A (PRIOR ART)
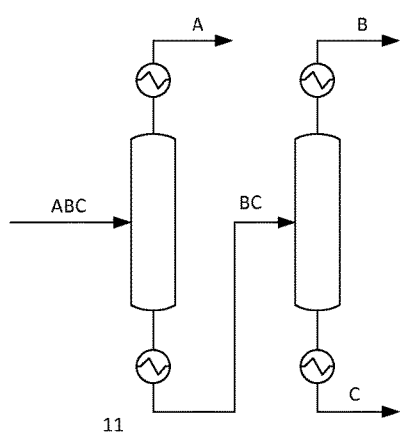
Fig. 1B (PRIOR ART)
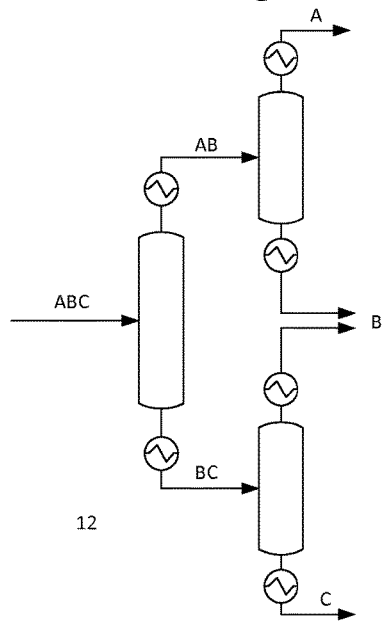
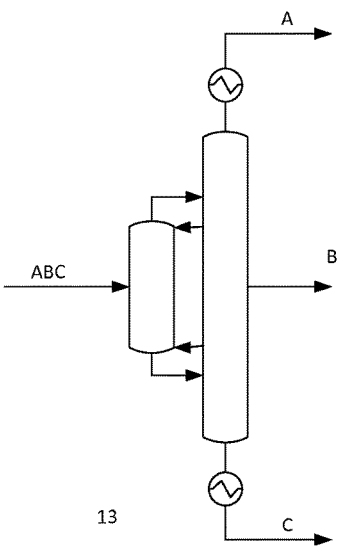
Fig. 1C (PRIOR ART)
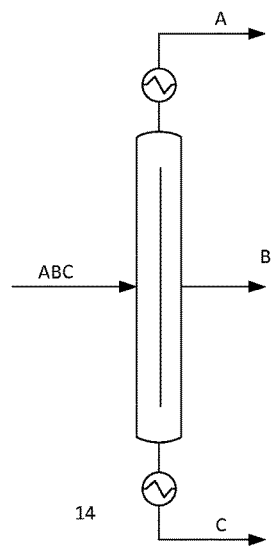
Fig. 1D (PRIOR ART)

METHOD AND APPARATUS FOR THE SEPARATION BY DISTILLATION OF A THREE- OR MULTI-COMPONENT MIXTURE

CROSS REFERENCE TO RELATED APPLICATIONS

This application is the U.S. National Phase of PCT Appln. No. PCT/EP2014/056055 filed Mar. 26, 2014, which claims priority to German Application No. 10 2013 207 282.1 filed Apr. 22, 2013, the disclosures of which are incorporated in their entirety by reference herein.

BACKGROUND OF THE INVENTION

1. Field of the Invention

The invention relates to the rectification or distillation of a mixture of three or more components, that is, to a process for distillative separation of a given mixture into its constituent parts, and also to an apparatus for carrying out the process through suitable coupling of distillation columns.

2. Description of the Related Art

Distillative processes are commonly used in chemical process technology to thermally separate mixtures of different relative volatilities and/or mutually soluble materials.

Various process variants may be used for the continuous distillative separation of multicomponent mixtures.

In the simplest case, a feed mixture composed of a low boiling fraction and a high boiling fraction is separated into its two fractions, a low boiling top fraction and a high boiling bottom fraction. In this case, the mixture to be separated is introduced between the bottom and the top of the distillation column. The feed inlet divides the column into a rectifying section and a stripping section. The high boiling fraction is removed from the column in the bottoms. Part of the concentrate is evaporated using a heating unit (e.g. a natural circulation evaporator) installed in the bottom region. The low boiler rises up inside the column as vapor, is withdrawn from the top of the column, and is condensed in a condenser. A portion of the condensate is recycled back into the column and flows downward in countercurrent to the ascending vapors (reflux).

However, in the case of separation of feed mixtures consisting of a multicomponent mixture of more than two fractions, several conventional distillation columns must be used.

FIGS. 1A-1D show possible systems for separating a three component mixture ABC comprising low boiler A, medium boiler B, and high boiler C.

Therein, 11 in FIG. 1A shows the a-path, 12 in FIG. 1B shows coupling so as to allow material transfer with pre-separation, 13 in FIG. 1C shows coupling so as to allow material transfer with a pre-column, and 14 in FIG. 1D shows a conventional dividing wall column.

In the case of the a-path 11 shown in FIG. 1A, the low boiler A is removed as top product in a first column. The bottom fraction is a mixture composed of a medium boiler B and a high boiler C, which is separated into the two pure substances B and C in a downstream column.

In the case of coupling so as to allow material transfer with pre-separation (a/c-path) 12 shown in FIG. 1B, the separation in the first column is effected in such a way that the top product contains no high boiler C and the bottom product contains no low boiler A. Thus, the separation of the low boiler A and the high boiler C is carried out. The medium boiler B is present in both the top fraction as well as the bottom fraction. Both fractions AB and BC are separated into the pure products A, B, and C, with each fraction being separated in a separate downstream column. Variant 12 thus requires three separation steps.

In the case of the c-path (not shown), C is removed as pure bottom product in the first column and mixture AB is transferred to the second column as the top product, typically as a vapor.

When separating a three component mixture, the choice of a suitable path (a-path, c-path, a/c path) depends on the composition of the input.

When the content of low boiler A is high, the a-path is preferred. By contrast, preference should be given to the c-path when the content of high boiler C is high. When the proportion of medium boiler B is high, the a/c path is preferably selected.

In the case of coupling so as to allow material transfer with a pre-column 13 shown in FIG. 1C, both columns are coupled so as to allow material transfer (thus two-fold coupling so as to allow material transfer; Petlyuk configuration).

An alternative to the coupling of two or more distillation columns are dividing wall columns, i.e. columns that prevent transverse mixing of liquid streams and vapor streams in sections of the column by providing a vertical dividing wall disposed in the longitudinal direction of the column. The vertical dividing wall runs along a portion of the column height and divides the cross-section into two sections to the left and to the right of the dividing wall.

As illustrated in FIG. 1D, 14 shows a conventional dividing wall column in which the high boiler is discharged as bottoms, the medium boiler is discharged via the sidestream takeoff, and the low boiler is discharged via the top stream. With such a column it is possible, for example, to separate a three component mixture into its three pure component parts in a single column while two conventional columns are normally required.

The dividing wall disposed in the longitudinal direction of the column divides the column interior into a feed section, a removal section, an upper combined column section (rectifying section), and a lower combined column section (stripping section).

The feed inlet for the mixture to be separated is generally positioned in a central region of the feed section (left of the dividing wall) between an upper and a lower region of the feed section. It is also possible to provide one or more further inlets between an upper and a lower region of the feed section.

In the removal section—right of the dividing wall—one or more sidestream takeoffs are disposed between an upper and a lower region. It is also possible to provide a further sidestream takeoff between the lower and the lowest region of the removal section.

WO 2009/092682 A1, the disclosure of which is incorporated herein in its entirety, discloses a process for distillative processing of 1,5,9-cyclododecatriene (CDT), and also an apparatus for carrying out the process. The object is achieved by starting from a process for distillative processing of crude CDT obtained by trimerisation of butadiene. Dividing wall columns are used for the distillative separation of the crude CDT formed as a multicomponent mixture. The dividing wall, which may be composed of a metal sheet or two or more individual metal sheets joined together divides the column longitudinally in its middle section into a feed section and a removal section. With regard to the separating internals that may be used in the dividing wall column, both random packings as well as structured packings, or separating trays are useful. It is possible to configure the dividing wall as loosely inserted segments.

U.S. Pat. No. 6,884,324 B2, the disclosure of which is incorporated herein in its entirety, discloses a column having two distillation stages for concentrating phthalic anhydride (PA), in which the distillative removal of the low boilers in the crude PA is carried out in the first distillation stage and the removal of the high boilers from the pure PA is carried out in the second distillation stage, wherein both distillation stages are disposed alongside one another and completely separated from one another by a vertically disposed wall, wherein the bottom of the first distillation stage is connected to the bottom of the second distillation stage. The bottom of the first distillation stage can be connected to the bottom of the second distillation stage via an overflow tube. Likewise, the bottom of the first distillation stage can be connected to the bottom of the second distillation stage via a pump.

It is known in the prior art to use two or more distillation columns, performing different separation functions in an assemblage, or to use one dividing wall column, for separating multicomponent mixtures.

It would be desirable to minimize the energy consumption of the entire distillation assembly. When exclusively individual separation functions are examined, barriers to this goal are encountered.

At best, the use of new internals which allow a lower pressure drop and thus a minimized exergy loss with high separation performance may be considered, and also an optimized control system (process control).

A further possible option is vapor compression, which is on account of its high capital costs and use of pure exergy (electricity), however, only cost-effective when the materials of the multicomponent mixture to be separated have a sufficiently high adiabatic exponent which would allow a large temperature change with relatively low expenditure on compression.

If low value waste heat is available at the production site under consideration, then the use of this waste heat as a heating medium for the distillation is generally preferred over vapor compression using pure exergy (electricity).

A greater variety of options is offered by measures such as coupling so as to allow heat transfer (integrated heat system via heat exchangers), through which the specific energy usage may be reduced.

US 2012/048719 A1, the disclosure of which is incorporated herein in its entirety, discloses a process for thermally separating silane mixtures comprising silanes selected from alkylchlorosilanes and hydrogenchlorosilanes in a distillation apparatus, in which at least a portion of the heat for heating the distillation apparatus is transferred from vapors of a further distillation apparatus and in which a silane product having impurity levels of no more than 200 ppm is obtained. A disadvantage of this process is the necessary pressure stepping if there is no inherent temperature spread through the mixture of materials to be separated. Furthermore, at low temperature differences between the heating side and the product side, a large surface area of the intermediate heat exchanger may be required.

When using the dividing wall columns previously described, the total savings of about 30% may be realized compared to a conventional series connection of two columns, based on running costs and capital costs. Thus, dividing wall columns are generally preferred in comparison to the conventional interconnection of distillation columns.

However, dividing wall columns must generally be built with larger dimensions than the corresponding individual apparatuses that they are to replace. The overall height of the dividing wall column thus corresponds to at least the overall height of one of the individual apparatuses and at most the sum of the overall heights of the individual apparatuses. Dependent on the hydraulic loading, the diameter of the dividing wall column equates to at least the smallest diameter of the individual apparatuses and at most the larger diameter of the individual apparatuses. Depending on the separation function (multicomponent mixture), extreme overall heights, large column diameters and thus high capital costs can result, which is disadvantageous. An objective of the invention results from this set of problems.

SUMMARY OF THE INVENTION

The object of the invention is achieved by a process for distillative separation of a mixture of three or more components comprising at least one low boiler, at least one medium boiler and at least one high boiler, wherein the mixture of three or more components is fed to a first column by means of which the at least one high boiler is removed as bottom fraction and a top fraction is fed to a second column, wherein in the second column the at least one medium boiler is removed via a sidestream takeoff and the at least one low boiler is removed as top fraction, and also a bottom takeoff stream from the second column is fed back to the first column as reflux, wherein both distillation columns have vertical dividing walls.

The object is also achieved by an apparatus for distillative separation of a mixture of three or more components, comprising two distillation columns coupled to one another so as to allow material transfer, in which vapors of a first distillation column are communicatively connected to the bottom of a second distillation column and bottom takeoff streams of the second distillation column are communicatively connected to a reflux section of the first distillation column, wherein both distillation columns have vertical dividing walls, wherein the second column has one or more sidestream takeoffs below the top takeoff and above the bottom takeoff.

BRIEF DESCRIPTION OF THE FIGURES

FIGS. 1A-1D show interconnections of two or more columns and also a dividing wall column according to the prior art.

DETAILED DESCRIPTION OF THE PREFERRED EMBODIMENTS

Figure 2:
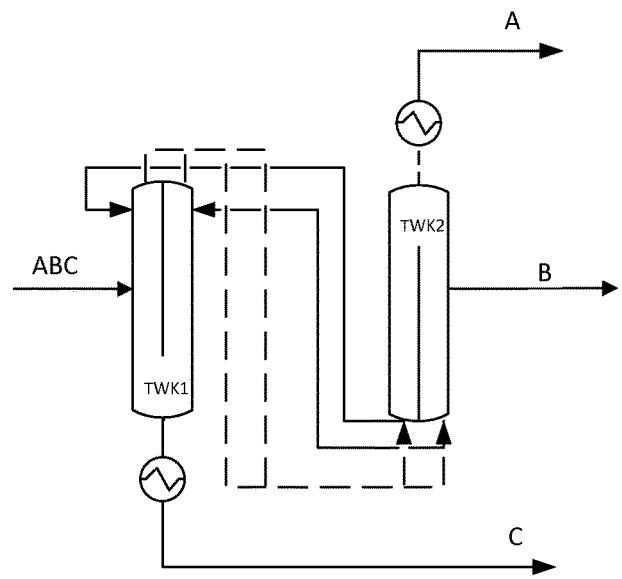
FIG. 2 shows the interconnection of two columns provided with dividing walls according to the invention.

The invention provides for coupling of distillation columns with one another so as to allow material transfer. In addition, vertical dividing walls are incorporated in each of the distillation columns.

The coupling so as to allow material transfer achieves an adding of the number of theoretical plates of the two columns.

Thus if two identically constructed columns are used, a doubling of the number of theoretical plates results.

The coupling so as to allow material transfer is accomplished in that each of the columns has at least two linkages with the respective other column at spatially separate locations.

Two such columns coupled so as to allow material transfer are equivalent to a single dividing wall column regarding energy requirements. Large energy savings can thus be realized, where, however, lower capital costs are incurred in comparison to the new acquisition of a conventional single dividing wall column since conventional pre-existing distillation columns can be converted into dividing wall columns in the context of a revamp and interconnected with one another in such a way that the two mentioned distillation columns provided with dividing walls perform the function of a prior art dividing wall column.

The columns coupled so as to allow material transfer may each be equipped with a dedicated evaporator and/or condenser.

The low boiler fraction and the high boiler fraction may be removed from different columns. The operating pressures of the columns are adjusted in such a way that the prescribed direction of flow is maintained. It is also possible to partially or completely evaporate the bottom stream of the first column in an evaporator and subsequently feed it to the second column in biphasic form or in the form of a gaseous stream and a liquid stream.

The mixture of three or more components is preferably a mixture comprising chlorosilanes or a mixture comprising methylchlorosilanes. Preference is given to mixtures from the TCS synthesis or the MCS synthesis (TCS=trichlorosilane, MCS=methylchlorosilane), or from the deposition of polycrystalline silicon. Preference is given to a mixture composed of chlorosilanes comprising TCS, STC, DCS, and also traces of further impurities (methylchlorosilanes, hydrocarbons, high boilers) as is obtained via the reaction of commercially available metallurgical silicon with HCl in a fluidized-bed reactor at 350-400° C.

In an assembly for producing polycristalline silicon, TCS is generated as crude silane either from metallurgical silicon and HCl or from metallurgical silicon with $STC/H_2$ (STC=silicon tetrachloride) in a fluidized-bed reactor. Subsequently, the crude silane is purified by distillation/purification to form TCS. Polycrystalline silicon is deposited from the purified TCS, whereupon, inter alia, STC is formed. The subsequent utilization of the STC (e.g. via hydrogenation to form trichlorosilane or by combustion to produce finely divided silica or silicic esters) is common.

During the deposition of polycrystalline silicon from a mixture of chlorosilane, in particular TCS, and hydrogen, a fraction of high boiling chlorosilanes is formed in addition to STC. The term "high boiling chlorosilanes" describes compounds composed of silicon, chlorine, optionally hydrogen, oxygen, and carbon and having a boiling point higher than that of STC (57° C. at 1013 hPa). Preference is given to the disilanes $H_nCl_{6-n}Si_2$ (n=0-4) and higher oligo(chloro) silanes preferably having 2 to 4 Si atoms, and also to the disiloxanes $H_nCl_{6-n}Si_2O$ (n=0-4) and higher siloxanes preferably having 2 to 4 Si atoms including cyclic oligosiloxanes and also their methyl derivatives.

The residues (high boilers) of the Müller-Rochow process are principally tetrachlorodimethyldisilane, trichlorotrimethyl-disilane and dichlorotetramethyldisilane, that is methylchloro-disilanes of the general composition $Me_{6-x}Cl_xSi_2$. These can be treated with metallurgical silicon and HCl at a temperature of at least 300° C. TCS and STC are formed in the process.

The high boilers in offgas from the deposition of polycrystalline silicon (Siemens process) are mainly chlorodisilanes of the general composition $H_{6-x}Cl_xSi_2$ and, as the case may be, chlorodisiloxanes $H_{6-x}Cl_xSi_2O$. In addition, the offgases comprise TCS, STC, and DCS.

The invention and its differences compared to the prior art are illustrated below with the aid of figures.

FIG. 2 shows a dividing wall column via coupling of two existing distillation columns TWK1 and TWK2 according to the invention. The invention provides for coupling of the existing distillation columns so as to allow material transfer, i.e. feeding the vapors of one column directly to the column bottom of the second column and also providing the bottom takeoff stream and/or bottom takeoff streams of the other column to the first column as reflux. The two individual apparatuses are equipped with the necessary dividing walls, internals, and sidestream takeoffs in the context of the conversion. The design according to FIG. 2 is energetically equivalent to the dividing wall column 14 in FIG. 1D. Compared to new investment, the conversion can be carried out with reduced capital expenditure.

The distillation columns are preferably equipped with separating plates of different types such as separating trays (e.g. sieve trays, fixed valves), random packings (packing bodies), or structured packings. The internals are critical determinants of separation performance and also of the pressure drop over the distillation columns.

The mentioned distillation columns preferably have 1-200 theoretical plates, where the number of theoretical plates necessary is dependent on the quality/degree of contamination of the starting mixture to be separated, the specified purity requirements for the target product, and also on the relative volatility of the individual components of the multicomponent mixture (with respect to the key components).

The distillation columns are preferably operated at an offgas pressure of from −1 to +10 bar and a boiling temperature range of from −20 to +200° C.

Regarding a distillation assembly composed of two or more individual apparatuses, the offgas pressures can—bearing in mind economic aspects—be selected independently of one another. The mentioned distillation columns/individual apparatuses are also preferably equipped with one or more evaporator systems for supplying the heat energy.

In a conventional evaporator system, one or more heat generators are flanged to the column body of an individual apparatus via connectors/adapters. The heat generator can also be designed in a wide variety of forms from a process technology standpoint—preferably, however, it is designed as a natural circulation evaporator.

The column body is preferably equipped with a further connection for a second evaporator system.

If two distillation columns are coupled to one another as in FIG. 2, then at least one vapor tube of the first column is directly flanged to the column body of the second column. An existing flange connection on the column body can, where present, be used for such purpose. Should this connection be absent, then it must be retrofitted.

The vapor tube is preferably designed as a double tube. This allows heating by the bottom takeoff stream of a different column in the assembly. Condensation in the vapor tube can thereby be avoided.

The bottom takeoff stream of the second column is used for the reflux of the first column. To this end, for example, the reflux pumps of the first column can be connected to the bottom takeoff of the second column, as long as the pumps prove useful.

Preferred heat transfer agents for the evaporation are water vapor and/or thermal oils of various pressure and temperature ratings. The choice of the various operating materials for the evaporation is determined primarily by economic aspects and also by availability.

It is preferred that the mentioned distillation columns/individual apparatuses are additionally equipped with one or more condensing systems for condensing the vapor to supply the reflux amount to the respective column.

In the first condensing stage, uncondensable vapor portions composed of components having low boiling points and/or inert gas are fed to a further condensing stage and/or a further workup/other use (preferably a scrubber system).

Preferred heat transfer agents for the condensation are cooling water and/or cooling brine of various pressure and temperature ratings. The choice of the various operating materials for the condensation is determined primarily by economic aspects and also by availability.

Operation as a dividing wall tandem column requires one or preferably two or more side stream takeoffs on one of the two columns, at which the target product is withdrawn when the target product is a pure medium boiler B.

The correct position on the circumference and height of the column body should be selected according to the thermodynamic design. If, according to this thermal design, the takeoff is located between the two columns, then the target product can be withdrawn from the reflux line "to the right of the dividing wall" of the one column.

Example and Comparative Example

Comparative Example—Conventional Interconnection

Figure 3:
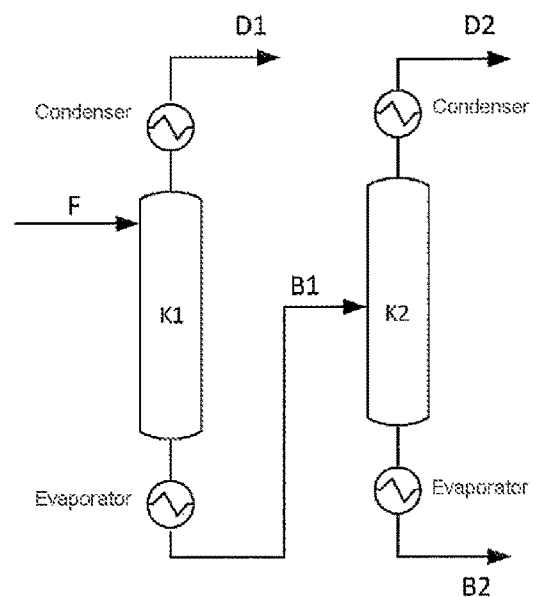
FIG. 3 shows a conventional interconnection of distillation columns composed of a stripping column with evaporator and condenser and also a second distillation column with evaporator and condenser.

FIG. 3 shows a conventional distillation arrangement composed of a stripping column including an evaporator and a condenser and also a rectifying column including an evaporator and a condenser.

The material stream F is composed of a chlorosilane-containing mixture having a low boiler fraction, medium boiler fraction, and high boiler fraction. In column K1, the low boiler fraction is removed via the material stream D1. The material stream B1 is fed into the second column K2 in which the high boiler fraction is withdrawn via material stream B2 and in which the target product (medium boiler fraction) is withdrawn via material stream D2.

Table 1 shows the mass fractions of the individual components in the respective substreams according to the comparative example

TABLE 1

| Component | Material stream | | | | |
|---|---|---|---|---|---|
| | F | D1 | B1 | D2 | B2 |
| TCS | 99.5% | 90% | 99.9% | 99.99% | 99.99% |
| DCS | 0.5% | 10% | — | — | — |
| C1 | <10 ppmw | — | 10 ppmw | 1 ppmw | 300 ppmw |
| C2 | <0.5 ppmw | 10 ppmw | 0.04 ppmw | 0.04 ppmw | — |
| C3 | <10 ppmw | 20 ppmw | — | — | — |

C1-C3 are trace impurities such as methylchlorosilanes, hydrocarbons, and dopant compounds.

Example—Dividing Wall Tandem Column

Figure 4:
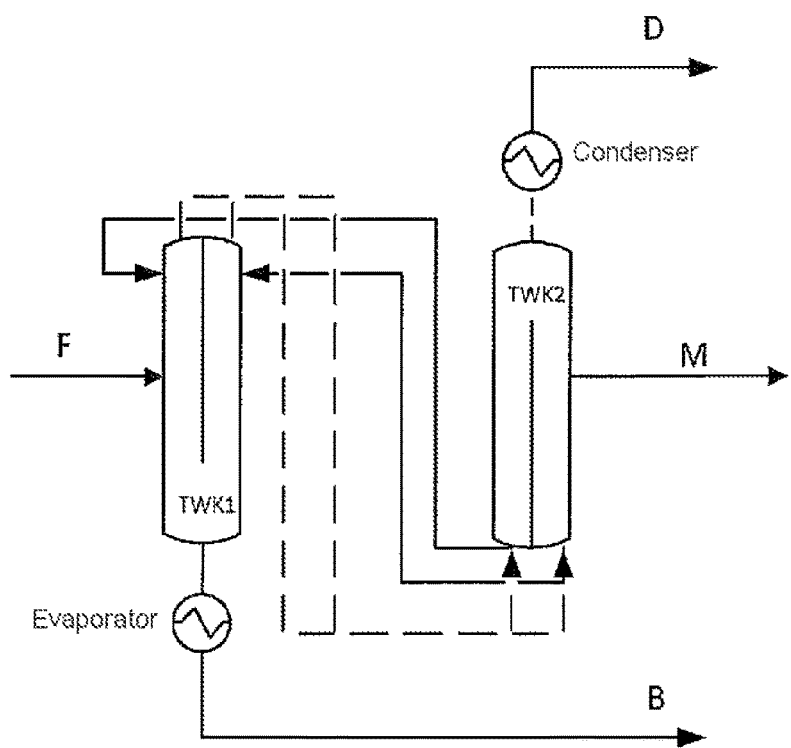
FIG. 4 shows a dividing wall tandem column with evaporator and condenser according to the invention, as used in the example.

FIG. 4 shows a preferred embodiment of a distillation column according to the invention comprising a first distillation column TWK1, designed as a dividing wall column, including an evaporator, and also a second distillation column TWK2, likewise designed as a dividing wall column, including a condenser.

The material stream F is composed of a chlorosilane-containing mixture having a low boiler fraction, a medium boiler fraction, and a high boiler fraction. In column TWK1, the high boiler fraction (comprising C1) is removed via material stream B. In the second column TWK2, the low boiler fraction (comprising DCS and C3) is withdrawn via material stream D and the target product (medium boiler fraction comprising TCS) is withdrawn via material stream M.

Table 2 shows the mass fractions of the individual components in the respective substreams according to the example.

TABLE 2

| Component | Material stream | | | |
|---|---|---|---|---|
| | F | D | B | M |
| TCS | 99.5% | 90% | 99.9% | 99.99% |
| DCS | 0.5% | 10% | — | — |
| C1 | <10 ppmw | — | 300 ppmw | 1 ppmw |
| C2 | <0.5 ppmw | 10 ppmw | — | 0.04 ppmw |
| C3 | <10 ppmw | 20 ppmw | — | — |

It can be seen in FIG. 4 that both an evaporator and a condenser are dispensed with compared to the comparative example.

The invention claimed is:

1. An apparatus for distillative separation of a mixture comprising three or more components, the apparatus comprising:
   a first distillation column coupled to a second distillation column to allow material transfer;
   at least one vapor tube of the first distillation column connected to a bottom of the second distillation column such that vapor(s) from the first distillation column are communicatively connected to the bottom of the second distillation column; and
   at least one bottom takeoff stream of the second distillation column connected to a reflux section of the first distillation column,
   wherein the first and the second distillation columns both have vertical dividing walls which in the first distillation column extend to a top end of the interior of the column, and which in the second distillation column extend to a bottom end of the interior of the column, the first distillation column having a combined lower stripping section and the second distillation column having a combined upper recitifying section, wherein the second distillation column has one or more sidestream takeoffs below a top takeoff stream and above the at least one bottom takeoff stream, and wherein at least the first distillation column comprises one or more evaporators for evaporating a liquid bottom stream.

2. The apparatus of claim 1, wherein the first and the second distillation columns have 1-200 theoretical plates.

3. The apparatus of claim 2, wherein both the first distillation column and the second distillation column comprise one or more evaporators for evaporating liquid bottom stream.

4. The apparatus of claim 1, wherein at least the second distillation column comprises one or more condensers for condensing vapor stream(s).

5. The apparatus of claim 2, wherein at least the second distillation column comprises one or more condensers for condensing vapor stream(s).

6. A method for distillative separation of a mixture comprising three or more components including at least one low boiler, at least one medium boiler, and at least one high boiler in an apparatus of claim 1, the method comprising:
feeding the mixture of three or more components to the first distillation column,
removing the at least one high boiler as a bottom fraction from the first distillation column;
feeding a top fraction of the first distillation column to the bottom of the second distillation column;
removing the at least one medium boiler via a sidestream takeoff from the second distillation column;
removing the at least one low boiler as a top fraction from the second distillation column; and
feeding a bottom takeoff stream from the second distillation column to the first distillation column as a reflux.

7. The method of claim 6, further comprising operating the first and the second distillation columns at an offgas pressure of from about −1 to 10 bar and a boiling temperature range of from about −20 to 200° C.

8. The method of claim 6, wherein the first and the second distillation columns comprise one or more evaporators that utilize water vapor or thermal oil(s) of various pressure and temperature ratings as heat transfer agents.

9. The method of claim 6, wherein the first and the second distillation columns comprise one or more condensers that utilize cooling water or cooling brine of various pressure and temperature ratings as heat transfer agents.

10. The method of claim 7, wherein the first and the second distillation columns comprise one or more condensers that utilize cooling water or cooling brine of various pressure and temperature ratings as heat transfer agents.

11. The method of claim 6, further comprising feeding uncondensable top stream component(s) from a first condensation stage to a second condensation stage and/or to a scrubber system.

12. The method of claim 7, further comprising feeding uncondensable top stream component(s) from a first condensation stage to a second condensation stage and/or to a scrubber system.

13. The method of claim 6, wherein the mixture comprising three or more components comprises chlorosilanes as the medium boiler.

14. The method of claim 7, wherein the mixture comprising three or more components comprises chlorosilanes as the medium boiler.

* * * * *